US007867490B2

(12) United States Patent
Carmeliet et al.

(10) Patent No.: US 7,867,490 B2
(45) Date of Patent: Jan. 11, 2011

(54) TREATMENT OF LIVER CIRRHOSIS AND ITS COMPLICATIONS

(75) Inventors: Peter Carmeliet, Blanden (BE); Isabelle Colle, Wetteren (BE); Anja Geerts, Verrebroek (BE)

(73) Assignees: VIB VZW, Zwijnaarde (BE); Life Sciences Research Partners VZW, Leuven (BE); Universiteit Gent, Ghent (BE)

( * ) Notice: Subject to any disclaimer, the term of this patent is extended or adjusted under 35 U.S.C. 154(b) by 0 days.

(21) Appl. No.: 11/922,702

(22) PCT Filed: Jun. 30, 2006

(86) PCT No.: PCT/EP2006/063762
§ 371 (c)(1),
(2), (4) Date: Dec. 21, 2007

(87) PCT Pub. No.: WO2007/003609
PCT Pub. Date: Jan. 11, 2007

(65) Prior Publication Data
US 2009/0111974 A1 Apr. 30, 2009

(30) Foreign Application Priority Data
Jun. 30, 2005 (EP) .................................. 05105923

(51) Int. Cl.
*A61K 39/395* (2006.01)
(52) U.S. Cl. .............. 424/130.1; 424/141.1; 424/142.1; 424/145.1
(58) Field of Classification Search ........................ None
See application file for complete search history.

(56) References Cited

U.S. PATENT DOCUMENTS

| 5,545,806 | A | 8/1996 | Lonberg et al. |
| 5,851,999 | A | 12/1998 | Ullrich et al. |
| 5,919,899 | A | 7/1999 | Persico et al. |
| 6,369,204 | B1 | 4/2002 | Kim et al. |
| 2002/0009750 | A1 | 1/2002 | Rockwell et al. |
| 2003/0180286 | A1* | 9/2003 | Carmeliet et al. ........ 424/130.1 |

FOREIGN PATENT DOCUMENTS

| JP | 2001/086982 | 4/2001 |
| WO | WO 84/03564 | 9/1984 |
| WO | WO 96/30046 | 10/1996 |
| WO | WO 97/15330 | 5/1997 |
| WO | WO 98/13071 | 4/1998 |
| WO | WO 99/24056 | 5/1999 |
| WO | WO 99/60846 | 12/1999 |
| WO | WO 01/85796 | * 11/2001 |
| WO | WO 01/85796 A2 | 11/2001 |
| WO | WO 03/000183 A2 | 1/2003 |
| WO | WO 03/103581 | 12/2003 |

OTHER PUBLICATIONS

Webster's II New Riverside University Dictionary, p. 933, 1994.*
Ahmed, A., et al., "Regulation of placental vascular endothelial growth factor (VEGF) and placenta growth factor (PlGF) and soluble Flt-1 by oxygen—a review," Placenta, (2000), vol. 21 Suppl A, S16-S24.
Bais, C., et al., "PIGF blockade does not inhibit angiogenesis during primary tumor growth," Cell, (2010), pp. 166-177, vol. 141.
Barillari, G., et al. "The basic residues of placenta growth factor type 2 retrieve sequestered angiogenic factors into a soluble form: implications for tumor angiogenesis," Am. J. Pathol., (1998), pp. 1161-1166, vol. 152.
Bernatchez, P.N., et al., Vascular endothelial growth factor effect on endothelial cell proliferation, migration, and platelet-activating factor synthesis is Flk-1-dependent, J. Biol. Chem., (1999), pp. 31047-31054, vol. 274.
Bicknell, R., et al. "1.Introduction / 2. In vivo models of angiogenesis. In Tumour Angiogenesis," (1997), pp. 1-18, (Oxford University Press).
Bottomley, M.J., et al., "Placenta growth factor (PIGF) induces vascular endothelial growth factor (VEGF) secretion from mononuclear cells and is co-expressed with VEGF in synovial fluid," Clin. Exp. Immunol., (2000), pp. 182-188, vol. 119.
Boulton, M., et al., "Placental growth factor localisation in diabetic retinas and preretinal membranes," Invest Ophthalmol. Vis. Sci., (1997), vol. 38, S965.
Brenchley, P.E., Angiogenesis in inflammatory joint disease: a target for therapeutic intervention, Clin. Exp. Immunol., (2000), pp. 426-429, vol. 121.

(Continued)

*Primary Examiner*—Phuong Huynh
(74) *Attorney, Agent, or Firm*—Foley & Lardner LLP

(57) ABSTRACT

The present invention relates to the field of liver diseases, more particularly to the field of portal hypertension and liver cirrhosis. The invention relates to the use of molecules which can inhibit the binding of placental growth factor (PIGF) to its receptor (VEGFR-1), such as monoclonal antibodies, for the manufacture of a medicament to treat liver cirrhosis, portal hypertension and its complications.

7 Claims, No Drawings

OTHER PUBLICATIONS

Carmeliet, P., "Basic Concepts of (Myocardial) Angiogenesis: Role of Vascular Endothelial Growth Factor and Angiopoietin," Curr. Intern. Cardiol. Rep. 1, (1999), pp. 322-335.

Carmeliet, P. "Gene targeting and gene transfer to unravel the molecular basis of the formation and disorders of blood vessels,"Verh K Acad Geneesk BeIg, (2000), pp. 31-68, vol. 62.

Carmeliet, P. et al., "Molecular analysis of blood vessel formation and disease," Am. J. Physiol, (1997), pp. H2091-H2104, vol. 273.

Carmeliet, P. et al., "Role of vascular endothelial growth factor and vascular endothelial growth factor receptors in vascular development," Curr. Top. Microbiol. Immunol., (1999), pp. 133-158, vol. 237.

Carmeliet, P. et al., "Transgenic mouse models in angiogenesis and cardiovascular disease," J. Pathol., (2000), pp. 387-405, vol. 190.

Carmeliet, P., "Mechanisms of angiogenesis and arteriogenesis," Nat. Med., (2000), pp. 389-395, vol. 6.

Carmeliet, P., "Molecular mechanisms of normal and pathologic angiogenesis: insights and therapeutic concepts from transgenic cells," Journal of Vascular Research, (2000), p. 79. vol. 37.

Carmeliet, P., et al., "Synergism between vascular endothelial growth factor and placental growth factor contributes to angiogenesis and plasma extravasation in pathological conditions," Nat. Med., (2001), pp. 575-583, vol. 7.

Chen,Y. et al., "Selection and analysis of an optimized anti-VEGF antibody: crystal structure of an affinity-matured Fab in complex with antigen," J. Mol. Biol., (1999), pp. 865-881, vol. 293.

Christinger, H.W. et al., "The crystal structure of placental growth factor in complex with domain 2 of vascular endothelial growth factor receptor-1," J. Biol. Chem., (2004), pp. 10382-10388, vol. 279.

Colucciello, M., "Diabetic retinopathy. Control of systemic factors preserves vision," Postgrad. Med., (2004), pp. 57-64, vol. 116.

Declerck, P.J., et al., "Generation of monoclonal antibodies against autologous proteins in gene-inactivated mice," J. Biol. Chem., (1995), pp. 8397-8400, vol. 270.

Dias, S., et al., "Inhibition of both paracrine and autocrine VEGF/ VEGFR-2 signaling pathways is essential to induce long-term remission of xenotransplanted human leukemias," Proc. Natl. Acad. Sci. U. S., (2001), pp. 10857-10862, vol. A 98.

Donnini, S., et al., Expression and localization of placenta growth factor and PIGF receptors in human meningiomas, J. Pathol., (1999), pp. 66-71, vol. 189.

Fidler, I.J., et al., "Biology of Cancer:Angiogenesis. In Cancer. Principles & Practice of Oncology, Lippincott Williams & Wilkins)," (2000), pp. 137-147.

Fischer, C., et al., "Anti-PIGF inhibits growth of VEGF(R)-inhibitor-resistant tumors without affecting healthy vessels," Cell, (2007), pp. 463-475, vol. 131.

Fischer, C., et al., "Anti-PIGF inhibits growth of VEGF(R)-inhibitor-resistant tumors without affecting healthy vessels," Cell, (2007), pp. 463-475, vol. 131—Supplementary Data.

Folkman, J., "Seminars in Medicine of the Beth Israel Hospital, Boston. Clinical applications of research on angiogenesis, "N. Engl. J. Med., (1995), pp. 1757-1763, vol. 333.

Griffioen, A.W., et al., "Angiogenesis: potentials for pharmacologic intervention in the treatment of cancer, cardiovascular diseases, and chronic inflammation," Pharmacol. Rev., (2000), pp. 237-268, vol. 52.

Guidi, A.J., et al., Expression of vascular permeability factor (vascular endothelial growth factor) and its receptors in endometrial carcinoma, Cancer, (1996), pp. 454-460, vol. 78.

Gura, T., "Systems for identifying new drugs are often faulty," Science, (1997), pp. 1041-1042, vol. 278.

Johnstone, A., et al., "Production of antibodies. In Immunochemistry in practice," Blackwell Scientific Publications, (1987), p. 30.

Hazelton, D.A., et al., "Vascular endothelial growth factor in ovarian cancer," Curr. Oncol. Rep. 1, (1999), pp. 59-63.

Hansma et al. "Recombinant human endostatin administered as a 28-day continuous intravenous infusion, followed by daily subcutaneous injections: a phase I and pharmacokinetic study in patients with advanced cancer," Annals of Oncology 16, 1695-1701 (2005).

Holm, P., et al., "Functional mapping and single chain construction of the anti-cytokeratin 8 monoclonal antibody TS1," Mol. Immunol., (2007), pp. 1075-1084, vol. 44.

Inoue, H., et al., "Mechanism of mustard oil-induced skin inflammation in mice," Eur. J. Pharmacol., (1997), pp. 231-240, vol. 333.

Iyer, S., et al., The crystal structure of human placenta growth factor-1 (PIGF-1), an angiogenic protein, at 2.0 A resolution, J. Biol. Chem., (2001), pp. 12153-12161, vol. 276.

Jain, R.K., et al., "alphaPIGF: a new kid on the antiangiogenesis block," Cell, (2007), pp. 443-445, vol. 131.

Johnstone, A., et al., "Production of antibodies. In Immunochemistry in practice, Blackwell Scientific Publications," (1987), p. 30.

Kanno, S., et al., Roles of two VEGF receptors, Flt-1 and KDR, in the signal transduction of VEGF effects in human vascular endothelial cells, Oncogene, (2000), pp. 2138-2146, vol. 19.

Katoh, R., et al., Expression of vascular endothelial growth factor (VEGF) in human thyroid neoplasms, Hum. Pathol., (1999), pp. 891-897, vol. 30.

Khaliq, A., et al., "Increased expression of placenta growth factor in proliferative diabetic retinopathy," Lab Invest, (1998), pp. 109-116, vol. 78.

Kohler, G., et al., "Continuous cultures of fused cells secreting antibody of predefined specificity," J. Immunol., (1975), pp. 2453-2455, vol. 174.

Laurin, N., et al., "Paget disease of bone: mapping of two loci at 5q35-qter and 5q31," Am. J. Hum. Genet., (2001), pp. 528-543, vol. 69.

Lou, K.-J., "PIGF point-counterpoint," SciBX, (2010), pp. 5-7, vol. 3.

Luttun, A., et al., "Loss of placental growth factor protects mice against vascular permeability in pathological conditions," Biochem. Biophys. Res. Commun., (2002), pp. 428-434, vol. 295.

MacCallum, R.M., et al., "Antibody-antigen interactions: contact analysis and binding site topography," J. Mol. Biol., (1996), pp. 732-745, vol. 262.

Maglione, D., et al., "Two alternative mRNAs coding for the angiogenic factor, placenta growth factor (PIGF), are transcribed from a single gene of chromosome 14," Oncogene, (1993), pp. 925-931, vol. 8.

Maglione, D., et al., Isolation of a human placenta cDNA coding for a protein related to the vascular permeability factor, Proc. Natl. Acad. Sci. U. S., (1991), pp. 9267-9271, vol. A 88.

Maragoudakis, M.E., "Introductory Comments. In Angiogenesis. From the molecular to integrative pharmacology, M.E. Maragoudakis, ed. Kluwer Academic/Plenum Publishers," (2000), pp. 1-4.

Mayr-Wohlfart, U., et al., Vascular endothelial growth factor stimulates chemotactic migration of primary human osteoblasts, Bone, (2002), pp. 472-477, vol. 30.

Migdal, M., et al., Neuropilin-1 is a placenta growth factor-2 receptor, J. Biol. Chem. (1998), pp. 22272-22278, vol. 273.

Miller, K.D., Issues and challenges for antiangiogenic therapies, Breast Cancer Res. Treat., (2002), pp. S45-S50, vol. 75 Suppl 1.

Mitamura, Y., et al., "Placenta growth factor and vascular endothelial growth factor in the vitreous of patients with proliferative vitreoretinopathy," Clin. Experiment. Ophthalmol., (2005), pp. 226-227, vol. 33.

Mixed results on new cancer drug. Preliminary studies show endostatin is safe, may help some patients. MSNBC News Services (online) / Health Bulletin Board . Sep. 11, 2000.

Mueller, B.M., et al., "Expression of tissue factor by melanoma cells promotes efficient hematogenous metastasis," Proc. Natl. Acad. Sci. U. S.A., (1992), pp. 11832-11836, vol. 89.

Nicol, D., et al., "Vascular endothelial growth factor expression is increased in renal cell carcinoma," J. Urol., (1997), pp. 1482-1486, vol. 157.

Niida, S., et al., "Vascular endothelial growth factor can substitute for macrophage colony-stimulating factor in the support of osteoclastic bone resorption," J. Exp. Med., (1999), pp. 293-298, vol. 190.

Nomura, M., et al., "Placenta growth factor (PIGF) mRNA expression in brain tumors," J. Neurooncol., (1998), pp. 123-130, vol. 40.

Oliver, S.J., et al., Suppression of collagen-induced arthritis by an angiogenesis inhibitor, AGM-1470, in combination with cyclosporin: reduction of vascular endothelial growth factor (VEGF), Cell Immunol., (1995), pp. 196-206, vol. 166.

Paleolog, E.M., et al., "Angiogenesis in arthritis: role in disease pathogenesis and as a potential therapeutic target," Angiogenesis., (1998), pp. 295-307, vol. 2.

Paques, M., et al., Growth factors and diabetic retinopathy, Diabetes Metab, (1997), pp. 125-130, vol. 23.

Park, J.E., et al., "Placenta growth factor. Potentiation of vascular endothelial growth factor bioactivity, in vitro and in vivo, and high affinity binding to Flt-1 but not to Flk-1/KDR," J. Biol. Chem., (1994), pp. 25646-25654, vol. 269.

Parry, T.J., et al., "Bioactivity of anti-angiogenic ribozymes targeting Flt-1 and KDR mRNA," Nucleic Acids Res. (1999) 27, 2569-2577.

De Pascalis, R., et al., "Grafting of "abbreviated" complementarity-determining regions containing specificity-determining residues essential for ligand contact to engineer a less immunogenic humanized monoclonal antibody," J. Immunol., (2002), pp. 3076-3084, vol. 169.

Queen, C., et al., A humanized antibody that binds to the interleukin 2 receptor, Proc. Natl. Acad. Sci. U. S.A., (1989), pp. 10029-10033, vol. 86.

R&D Systems, Inc. Monoclonal anti-human PlGF antibody. 2007, pp. 1-2.

R&D Systems, Inc. Biotinylated Anti-mouse PlGF-2 Antibody. 1999, p. 1.

R&D Systems, Inc. Monoclonal anti-mouse PlGF-2 antibody. 1999, p. 1.

Robinson, G.S., et al., Nonvascular role for VEGF: VEGFR-1, 2 activity is critical for neural retinal development, FASEB J., (2001), pp. 1215-1217, vol. 15.

Rudikoff, S., et al., "Single amino acid substitution altering antigen-binding specificity," Proc. Natl. Acad. Sci. U. S.A., (1982), pp. 1979-1983, vol. 79.

Ryan, A.M., et al., Preclinical safety evaluation of rhuMAbVEGF, an antiangiogenic humanized monoclonal antibody, Toxicol. Pathol., (1999), pp. 78-86, vol. 27.

Skolnick, J., et al., "From genes to protein structure and function: novel applications of computational approaches in the genomic era," Trends Biotechnol., (2000), pp. 34-39, vol. 18.

Takahashi, A., et al., "Markedly increased amounts of messenger RNAs for vascular endothelial growth factor and placenta growth factor in renal cell carcinoma associated with angiogenesis," Cancer Res., (1994), pp. 4233-4237, vol. 54.

Vajdos, F.F., et al., Comprehensive functional maps of the antigen-binding site of an anti-ErbB2 antibody obtained with shotgun scanning mutagenesis, J. Mol. Biol., (2002), pp. 415-428, vol. 320.

Van De Veire, S., et al., "Further pharmacological and genetic evidence for the efficacy of PlGF inhibition in cancer and eye disease," Cell, (2010), pp. 178-190, vol. 141.

Viglietto, G., et al., "Upregulation of vascular endothelial growth factor (VEGF) and downregulation of placenta growth factor (PlGF) associated with malignancy in human thyroid tumors and cell lines," Oncogene (1995) 11, 1569-1579.

Viglietto, G., et al., (1996). Neovascularization in human germ cell tumors correlates with a marked increase in the expression of the vascular endothelial growth factor but not the placenta-derived growth factor. Oncogene 13, 577-587.

Weindel, K., et al., "Detection and quantification of vascular endothelial growth factor/vascular permeability factor in brain tumor tissue and cyst fluid: the key to angiogenesis?, " Neurosurgery (1994) 35, 439-448.

Wu, H., et al., "Humanization of a murine monoclonal antibody by simultaneous optimization of framework and CDR residues," J. Mol. Biol. (1999) 294, 151-162.

Yonekura, H., et al., "Placenta growth factor and vascular endothelial growth factor B and C expression in microvascular endothelial cells and pericytes. Implication in autocrine and paracrine regulation of angiogenesis," J. Biol. Chem. (1999) 274, 35172-35178.

Ziche, M., et al., "Placenta growth factor-1 is chemotactic, mitogenic, and angiogenic," Lab Invest 76, (1997) 517-531.

* cited by examiner

TREATMENT OF LIVER CIRRHOSIS AND ITS COMPLICATIONS

This application is the U.S. national phase of International Application No. PCT/EP2006/063762 filed 30 Jun. 2006 which designated the U.S. and claims priority to EP 05105923.6 filed 30 Jun. 2005, the entire content of each of which is hereby incorporated herein by reference.

FIELD OF THE INVENTION

The present invention relates to the field of liver diseases, more particularly to the field of portal hypertension and liver cirrhosis. The invention relates to the use of molecules which can inhibit the binding of placental growth factor (PlGF) to its receptor (VEGFR-1), such as monoclonal antibodies, for the manufacture of a medicament to treat liver cirrhosis, portal hypertension and its complications.

BACKGROUND OF THE INVENTION

The liver is the major metabolic control organ of the human body that comprises thousands of minute lobules (lobuli hepatis), the functional units of the organ. Liver tissue contains two major differentiated cell types: parenchymal cells (i.e., hepatocytes) and non-parenchymal cells. The complex functions of liver are exerted to a large extent by hepatocytes, whereas non-parenchymal cells such as Kupffer cells, Ito cells and liver sinusoidal endothelial cells (LSEC) play important roles in supporting and providing supplies to hepatocytes. The liver acts as a guardian interposed between the digestive tract and the rest of the body. A major hepatic function involves effective uptake, storage, metabolism and distribution to blood and bile large amounts of substances such as carbohydrates, lipids, amino acids, vitamins and trace elements. Another function of the liver is the detoxification of xenobiotic pollutants, drugs and endogenous metabolites, through both phase I (oxidation/reduction) and phase II (conjugation) mechanisms. Because of its essential role to life, liver dysfunction and diseases are often debilitating and life threatening. A number of acute or chronic pathological conditions are associated with structural and/or functional abnormalities of the liver. These include, but are not limited to, liver failure, hepatitis (acute or chronic), liver cirrhosis, toxic liver damage (for example alcohol), medicamentary liver damage, hepatic encephalopathy, hepatic coma and hepatic necrosis. Many chemical and biological agents, either therapeutic or purely harmful, can induce liver damages and thus are hepatotoxic. Liver cirrhosis results from the healing of a liver injury caused by viral or autoimmune hepatitis, alcohol abuse or other causes of liver damage. In liver cirrhosis, the scar tissue blocks the flow of blood through the liver and consequently this results in an increase in the pressure within the portal vein (the vein that carries the blood from the digestive organs to the liver) which is designated as portal hypertension. Increased pressure in the portal vein causes large veins (varices) to develop across the esophagus and stomach to bypass the blockage. The pressure in the varices increases and may rupture. Portal hypertension may also be caused by thrombosis, or clotting in the portal vein. Portal hypertension (PHT) in humans and laboratory animals is associated with a hyperkinetic circulation, vasodilation in the splanchnic territory and an hypersplenism. The hypersplenism can lead to an important pancytopenia.

Splanchnic vasodilation, the well-known increase in blood flow through the splanchnic organs draining into the portal venous system, is a major contributing factor for maintenance and aggravation of portal hypertension. The mechanisms by which portal hypertension induces this splanchnic vasodilation are not completely understood. Many theories have been proposed including an increase in circulating levels of vasodilator substances and reduced sensitivity to vasoconstrictors. Nevertheless, there is experimental evidence that splanchnic vasodilation in portal hypertension can be partially caused or maintained by structural vascular changes. In the venous circulation related to portal hypertension, portosystemic collaterals are formed which cause shunting of blood from the portal to the systemic circulation. Despite these collaterals, portal hypertension remains present. It has been shown recently that the formation of collateral vessels can be markedly inhibited by blockade of the vascular endothelial growth factor (VEGF) signalling pathway (Fernandez M et al Gastroenterology 2004; 126: 886-894). Our own experimental studies by intravital microscopy revealed also an increased angiogenesis in the peritoneal microcirculation of rats with PHT and cirrhosis. Evidence also shows that angiogenesis plays an important role in the development of liver fibrosis (Yoshiji H et al, Gut 2003: 52: 1347-1354; Lai W K et al, J Hepatol 2005; 42: 7-11; Medina J et al J Hepatol 2005; 42: 124-131). It has been shown that VEGF expression significantly increases during the development of liver fibrosis in experimental studies (Corpechot C et al, Hepatology 2002; 35:1010-21). Although recently an important role for placental growth factor (PlGF) has been described in pathological angiogenesis (patent application WO0185796, it is described that the use of VEGF-Receptor 1 agonists (such as PlGF) has a positive role for the treatment of cirrhosis (see patent application WO03103581, from Genentech, Inc.). The present invention surprisingly indicates the reverse and shows that molecules that can prevent the interaction between PlGF and its receptor, VEGF-R1 can be used for the manufacture of a medicament to treat cirrhosis and its complications such as portal hypertension and splanchnic vasodilatation.

AIMS AND DETAILED DESCRIPTION OF THE INVENTION

In previous studies, the PlGF gene was inactivated in the mouse genome via homologous recombination in embryonic stem (ES) cells (Carmeliet P., 2000, J. Pathol. 190, 387-405, Carmeliet P., 1999, Curr. Interv. Cardiol. Reports 1, 322-335 and Carmeliet P. and Collen D., 1999, Curr. Top. Microbiol. Immunol. 237, 133-158). PlGF (PlGF$^{-/-}$) deficient mice are viable and fertile, and did not exhibit spontaneous vascular defects. We have previously shown that growth of endothelial channels (angiogenesis), vascular maturation by smooth muscle cells (arteriogenesis) and vascular permeability are significantly impaired in adult PlGF$^{-/-}$ mice during a variety of conditions where pathological angiogenesis and oedema formation occurs (WO0185796). The present findings show that PlGF deficient mice are less vulnerable to the development of cirrhosis and its complications.

Thus in one embodiment the invention relates to the usage of molecules which comprise a region that can specifically bind to placental growth factor or to vascular endothelial growth factor receptor-1 and said molecules can be used to manufacture a medicament to suppress or prevent placental growth factor-induced liver cirrhosis and its complications. With "suppression" it is understood that suppression of cirrhosis and its complications can occur for at least 20%, 30%, 40%, 50%, 60%, 70%, 80%, 90% or even 100%. More specifically the invention relates to the use of molecules that can be used to neutralize the activity of PlGF by interfering with its synthesis, translation, dimerisation, receptor-binding and/ or receptor-binding-mediated signal transduction. By molecules it is meant peptides, proteins, organic molecules, mutants of the VEGFR-1, soluble receptors of VEGFR-1 and any fragment or homologue thereof having the same neutralizing effect as stated above. Also, the invention is directed to the use of antagonists of PlGF such as anti-PlGF antibodies and functional fragments derived thereof, anti-sense RNA and DNA molecules, RNA inhibition (RNAi molecules, also designated as siRNA molecules) and ribozymes that function to inhibit the translation of PlGF, all capable of interfering/or inhibiting the VEGFR-1 signal transduction. By synthesis it is meant transcription of PlGF. Small molecules can bind on the promoter region of PlGF and inhibit binding of a transcription factor or said molecules can bind said transcription factor and inhibit binding to the PlGF-promoter. By PlGF it is meant also its isoforms, which occur as a result of alternative splicing, and allelic variants thereof. As a result of alternative splicing, three PlGF RNAs encoding monomeric human PlGF-1, PlGF-2 and PlGF-3 isoform precursors containing 149, 179 and 219 amino acid residues, respectively, have been described. In normal mouse tissues, only one mouse PlGF mRNA encoding the equivalent of human PlGF-2 has been identified.

In a specific embodiment the invention uses an antibody against PlGF for the manufacture of a medicament to treat cirrhosis. In a particular embodiment said antibody against PlGF is used for the manufacture of a medicament to treat the complications of cirrhosis. In a specific embodiment the invention uses the murine monoclonal antibody against PlGF designated as Mab-PL5D11. This monoclonal antibody is available in the Department of Transgene Technology and Gene Therapy, U Z Gasthuisberg, Herestraat 49, B-3000 Leuven and is described in patent application WO0185796.

Complications of cirrhosis are herein defined as comprising portal hypertension, splanchnic vasodilatation, variceal hemorrhage, ascites, hypersplenism and portosystemic encephalopathy.

The term 'antibody' or 'antibodies' relates to an antibody characterized as being specifically directed against PlGF or VEGFR-1 or any functional derivative thereof, with said antibodies being preferably monoclonal antibodies; or an antigen-binding fragment thereof, of the F(ab')$_2$, F(ab) or single chain Fv type, or any type of recombinant antibody derived thereof. These antibodies of the invention, including specific polyclonal antisera prepared against PlGF or VEGFR-1 or any functional derivative thereof, have no cross-reactivity to others proteins. The monoclonal antibodies of the invention can for instance be produced by any hybridoma liable to be formed according to classical methods from splenic cells of an animal, particularly of a mouse or rat immunized against PlGF or VEGFR-1 or any functional derivative thereof, and of cells of a myeloma cell line, and to be selected by the ability of the hybridoma to produce the monoclonal antibodies recognizing PlGF or VEGFR-1 or any functional derivative thereof which have been initially used for the immunization of the animals. The monoclonal antibodies according to this embodiment of the invention may be humanized versions of the mouse monoclonal antibodies made by means of recombinant DNA technology, departing from the mouse and/or human genomic DNA sequences coding for H and L chains or from cDNA clones coding for H and L chains. Alternatively the monoclonal antibodies according to this embodiment of the invention may be human monoclonal antibodies. Such human monoclonal antibodies are prepared, for instance, by means of human peripheral blood lymphocytes (PBL) repopulation of severe combined immune deficiency (SCID) mice as described in PCT/EP 99/03605 or by using transgenic non-human animals capable of producing human antibodies as described in U.S. Pat. No. 5,545,806. Also fragments derived from these monoclonal antibodies such as Fab, F(ab)'$_2$ and ssFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies involved in the invention can be labeled by an appropriate label of the enzymatic, fluorescent, or radioactive type.

Small molecules, e.g. small organic molecules, and other drug candidates can be obtained, for example, from combinatorial and natural product libraries. To screen for said candidate/test molecules cell lines that express VEGFR-1 and VEGFR-2 may be used and the signal transduction is monitored as described in detail in the examples. Said monitoring can be measured using standard biochemical techniques. Other responses such as activation or suppression of catalytic activity, phosphorylation (e.g. the tyrosine phosphorylation of the intracellular domain of VEGFR-2) or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening. Inhibition of ligand binding to its cellular receptor may, via signal transduction pathways, affect a variety of cellular processes. Cellular processes under the control of the VEGFR-1/PlGF signalling pathway may include, but are not limited to, normal cellular functions, proliferation, differentiation, maintenance of cell shape, and adhesion, in addition to abnormal or potentially deleterious processes such as unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

Random peptide libraries, such as for example tetrameric peptide libraries, consisting of all possible combinations of amino acids attached to a solid phase support may be used to identify peptides that are able to bind to the ligand binding site of a given receptor or other functional domains of a receptor such as kinase domains (Lam K S et al., 1991, Nature 354, 82). The screening of peptide libraries may have therapeutic value in the discovery of pharmaceutical agents that act to inhibit the biological activity of receptors through their interactions with the given receptor. Identification of molecules that are able to bind to the VEGFR-1 or PlGF may be accomplished by screening a peptide library with recombinant soluble VEGFR-1 protein or PlGF protein. For example, the kinase and extracellular ligand binding domains of VEGFR-1 may be separately expressed and used to screen peptide libraries. In addition to using soluble VEGFR-1 molecules, in another embodiment, it is possible to detect peptides that bind to cell surface receptors using intact cells. The cells used in this technique may be either alive or fixed cells. The cells will be incubated with the random peptide library and will bind certain peptides in the library to form a "rosette" between the target cells and the relevant solid phase support/peptide. The rosette can thereafter be isolated by differential centrifugation or removed physically under a dissecting microscope.

In another embodiment transdominant-negative mutant forms of VEGF-receptors (e.g. a transdominant-negative receptor of VEGF-R1) can be used to inhibit the signal transduction of PlGF and hence to manufacture a medicament to treat liver cirrhosis or to treat the complications of liver cirrhosis. The use of said transdominant-negative mutant forms of VEGF-receptors is fully described in U.S. Pat. No. 5,851,999.

Also within the scope of the invention are oligoribonucleotide sequences that include anti-sense RNA and DNA molecules and ribozymes that function to inhibit the translation of VEGFR-1 mRNA or PlGF mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the VEGFR-1 or PlGF nucleotide sequence, are preferred. Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of VEGFR-1 or PlGF RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize anti-sense RNA constitutively or inducibly, depending on the promoter used, can be introduced stably into cell lines.

According to one embodiment, the invention provides methods for treating a pathological liver condition in a subject, more particularly liver fibrosis, more particularly liver cirrhosis and even more particularly the complications of liver cirrhosis. As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis.

In another embodiment the invention provides a method of treatment of cirrhosis or its complications in a subject comprising administering a pharmaceutical composition comprising means for modulating the interaction between placental growth factor and VEGF-Receptor 1 together with a pharmaceutical excipient.

In another embodiment the invention provides a method of treatment of cirrhosis or its complications in a subject comprising administering a pharmaceutical composition comprising means for modulating the interaction between placental growth factor and VEGF-Receptor 1 together with a pharmaceutical excipient wherein said means for is with an antibody against placental growth factor or an antibody against VEGF-Receptor 1 or a ribozyme against placental growth factor or a ribozyme against VEGF-Receptor 1 or a siRNA against placental growth factor or a siRNA against VEGF-Receptor 1 or an antisense molecule against placental growth factor or an antisense molecule against VEGF-Receptor 1.

The phrase "pathological liver condition" is used interchangeably with "liver disorder" or "liver disease" to indicate any structural and/or functional liver abnormalities. Non-limiting examples of pathological liver condition include those conditions associated with liver failure, hepatitis (e.g. hepatitis C), liver fibrosis, liver cirrhosis, toxic liver damage (for example alcohol), medicamentary liver damage, hepatic encephalopathy, hepatic coma or hepatic necrosis. Also vascular lesions of the liver, including thrombosis of the hepatic veins, occlusion of the hepatic venules or veno occlusive disease (VOD), and peliosis hepatitis, can be produced by drugs. In addition, lesions including sinusoidal dilation, perisinusoidal fibrosis, and hepatoportal sclerosis can occur. All of these lesions may lead to liver fibrosis and eventually towards liver cirrhosis. The term 'medicament to treat' relates to a composition comprising molecules as described above and a pharmaceutically acceptable carrier or excipient (both terms can be used interchangeably) to treat diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. The 'medicament' may be administered by any suitable method within the knowledge of the skilled man. The preferred route of administration is parenterally. In parental administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the protein, polypeptide, peptide of the present invention is given at a dose between 1 µg/kg and 10 mg/kg, more preferably between 10 µg/kg and 5 mg/kg, most preferably between 0.1 and 2 mg/kg. In one embodiment it is given as a bolus dose. Continuous infusion may also be used and includes continuous subcutaneous delivery via an osmotic minipump. If so, the medicament may be infused at a dose between 5 and 20 µg/kg/minute, more preferably between 7 and 15 µg/kg/minute. It is clear to the person skilled in the art that the use of a therapeutic composition comprising for example an antibody against PlGF for the manufacture of a medicament to treat cirrhosis or its complications can be administered by any suitable means, including but not limited to, parenteral, subcutaneous, intraperitoneal, intrapulmonary, and intranasal administration. Parenteral infusions include intramuscular, intravenous, intra-arterial, intraperitoneal, or subcutaneous administration. In addition, the therapeutic composition is suitably administered by pulse infusion, particularly with declining doses of the antibody. Preferably the therapeutic composition is given by injections, most preferably intravenous or subcutaneous injections, depending in part on whether the administration is brief or chronic.

In another embodiment antibodies or functional fragments thereof can be used for the manufacture of a medicament for the treatment of liver cirrhosis and the complications of liver cirrhosis. Preferentially said antibodies are humanized (Rader et al., 2000, J. Biol. Chem. 275, 13668) and more preferentially human antibodies are used as a medicament.

Another aspect of administration for treatment is the use of gene therapy to deliver the above mentioned anti-sense gene or functional parts of the PIGF gene or a ribozyme directed against the PIGF mRNA or a functional part thereof. Gene therapy means the treatment by the delivery of therapeutic nucleic acids to patient's cells. This is extensively reviewed in Lever and Goodfellow 1995; Br. Med Bull., 51, 1-242; Culver 1995; Ledley, F. D. 1995. Hum. Gene Ther. 6, 1129. To achieve gene therapy there must be a method of delivering genes to the patient's cells and additional methods to ensure the effective production of any therapeutic genes. There are two general approaches to achieve gene delivery; these are non-viral delivery and virus-mediated gene delivery.

The following examples more fully illustrate preferred features of the invention, but are not intended to limit the invention in any way. All of the starting materials and reagents disclosed below are known to those skilled in the art, and are available commercially or can be prepared using well-known techniques.

EXAMPLES

1. Animal Model of Portal Hypertension without Cirrhosis 1.1 Induction of Partial Portal Vein Ligation (PPVL) Mice Model Induction of pre-hepatic portal hypertension without cirrhosis is performed by partial portal vein ligation (PPVL). The mice are anaesthetised under isoflurane inhalation (Forene®, Abbott Laboratories Ltd, Kent, England). A midline abdominal incision is performed and the portal vein is separated from the surrounding tissue. A ligature (silk cut 5-0) is tied around both the portal vein and the adjacent 27-gauge blunt-tipped needle. Subsequent removal of the needle yields a calibrated stenosis of the portal vein. Afterwards, the abdominal wall is closed by suturing the abdominal muscle (silk cut 5-0) and clipping the skin.

It is generally accepted that 14 days is a period where the hyperdynamic syndrome has fully developed (Fernandez M, Gastroenterology (2004) 126: 886-894).

As a control group, we use sham-operated mice. In sham-operated mice, the abdominal cavity is opened and the portal vein is isolated, but no ligature is placed.

1.2 Induction of Portal Hypertension in PIGF Deficient Mice

A model for isolated portal hypertension (PHT) was induced in male (C57 BI/6) wild-type (wt) mice (n=6) or PIGF deficient mice (PIGF−/−) (n=6) by partial portal vein ligation (PPVL). Sham-operated wt (n=6) and PIGF−/− (n=6) mice were used as control groups. The VEGF and PIGF protein expressions in the mesentery were evaluated by ELISA. CD 31 expression, a marker for endothelial cell proliferation (neo-angiogenesis), was analysed by Western blotting and immunohistochemistry. A significantly higher VEGF and PIGF expression was observed in the mesentery of PPVL wt mice compared to Sham wt mice (p<0.05; p<0.05, respectively). The number of CD 31 positive endothelial cells was significantly higher in PPVL wt mice compared to Sham wt mice (p=0.004). However, a significantly lower number of CD 31 positive endothelial cells was observed in PPVL PIGF−/− mice compared to the PPVL wt group (p<0.05) and was comparable to levels seen in the Sham wt and Sham PIGF−/− groups. Spleen volume was significantly higher in the PPVL wt mice compared to the Sham wt mice (p<0.05). A significant reduction of this hypersplenism was observed in the PPVL PIGF−/− mice compared to the PPVL wt group.

Neo-angiogenesis was present in the mesentery of portal hypertensive mice, probably due to an upregulation of the vascular endothelial growth factor and the placental growth factor. The present study showed for the first time a role for PIGF in the increased mesenteric angiogenesis of portal hypertensive mice. PIGF can therefore contribute to the splanchnic vasodilation. The significant reduction in the spleen volume in PPVL PIGF−/− shows that there is a reduction in the splanchnic vasodilation compared to their wt mice.

1.3. Reduction of Portal Hypertension with Anti-PIGF Antibody

The delivery of anti-PIGF antibody (1000 μg/kg BW anti-PIGF intraperitoneally delivered every two days) in this group starts on the day of induction of PPVL till the 14$^{th}$ day after PPVL induction.

Four groups were included: PPVL group treated with anti-PIGF (n=6) or vehicle (n=6) and Sham-operated mice treated with anti-PIGF (n=6) or vehicle.

As previously mentioned, the spleen volume was significantly higher in the PPVL group compared to the Sham mice. This hypersplenism was significantly reduced in the PPVL group treated with anti-PIGF compared to their placebo group (p<0.05), indicating a reduced development of the splanchnic vasodilation.

The effect of anti-PIGF on collateral formation and hyperdynamic circulation in PPVL mice is currently evaluated.

2. Animal Models of Cirrhosis with Portal Hypertension 2.1 Common Bile Duct Ligation (CBDL) Model 2.1.1 Induction of CBDL Model Secondary biliary liver cirrhosis can be induced in experimental animals by common bile duct ligation (CBDL). In brief, under isoflurane inhalation (Forene®, Abbott Laboratories Ltd, Kent, England), a midline abdominal incision is made and the common bile duct is isolated (Fickert et al, Gastroenterology 2002; 123: 1238-1251). The common bile duct is occluded with a double ligature of a non-resorbable suture (silk cut 7-0). The common bile duct is resected between the two ligatures. Closure of the abdominal wall is done by suturing abdominal muscle (silk cut 5-0) and clipping the skin. An intramuscular injection of buprenorphine (Temgesic®, 0.1 ml/kg/12 hours) is given during a period of 48 hours after surgery to provide a good post-operative analgesia. In about 5 weeks after surgery, the mice have developed cirrhosis. Sham-operated mice were used as control groups. In sham-operated mice, the abdominal cavity is opened and the common bile duct is isolated, but no ligature is placed.

2.1.2 Induction of CBDL Model in PIGF Deficient Mice

CBDL model is induced in male (C57 BI/6) wild-type (wt) mice or PIGF deficient mice (PIGF−/−). Sham-operated wt and PIGF−/− mice were used as control groups.

A significantly higher VEGF and PlGF expression was observed in the mesentery of CBDL wt mice compared to Sham wt mice ($p<0.05$; $p<0.05$, respectively). Development of ascites was significantly lower in the CBDL PlGF−/− mice compared to their wt mice ($p<0.05$).

The progress of cirrhosis and other complications (especially varices formation) is monitored as described in materials and methods.

2.1.3 Regression of cirrhosis with Portal Hypertension with Anti-PlGF Antibody

At this time point 1000 µg/kg BW of anti-PlGF antibody is intraperitoneally administered every two days during two weeks in the CBDL and Sham mice. The regression of the progress of cirrhosis and its complications is monitored.

2.2 Carbon Tetrachloride ($CCl_4$) Model 2.2.1. Induction of $CCl_4$ Model

The intoxication of the liver with $CCl_4$ is a model for micronodular cirrhosis with characteristics mimicking human alcoholic cirrhosis. Cirrhosis is induced by subcutaneous injection with 1 mg/kg body weight of $CCl_4$ (Merck, Darmstadt, Germany) dissolved in an equal volume of olive oil twice weekly. 5% alcohol is added to the drinking water of the mice. Controls receive 1 mg/kg pure olive oil twice weekly. After three weeks of $CCl_4$ administration there is a beginning of liver fibrosis. In about 16 weeks after CCL4 induction the mice have developed cirrhosis 2.2.2. Induction of $CCl_4$ Model in PlGF Deficient Mice This model is induced in male (C57 Bl/6) wild-type (wt) mice or PlGF deficient mice (PlGF−/−). The progress of cirrhosis and its complications is monitored as described in materials and methods.

2.2.3. Regression of Cirrhosis with Portal Hypertension with Anti-PlGF Antibody

In about 16 weeks after CCL4 induction the mice have developed cirrhosis. At this time point 1000 µg/kg BW of anti-PlGF antibody is intraperitoneally administered every two days during 2 weeks. The regression of the progress of cirrhosis and its complications is monitored.

Materials and Methods

Animals

C57 BL/6 mice with targeted disruption of PlGF (PlGF−/−) and the corresponding WT mice (PlGF+/+) are used. The Ethical Committee of experimental animals at the Faculty of Medicine, Ghent University, Belgium, approves the protocols.

Flow Measurements: In Vivo Measurement of Mesenteric Blood Flow and Portal Venous Inflow An ultrasonic blood flow probe is placed around the mesenteric artery or portal vein that allows in vivo monitoring (Transonic Systems Inc., Ithaca, N.Y., USA) of either the mesenteric artery blood flow or portal venous inflow (Colle et al, Liver Int 2004; 24: 63-8; Colle et al, Eur J Gastroenterol Hepat 2004; 16: 139-145).

Measurement of Portal Venous Pressure

The portal venous pressure is measured in each mouse by cannulation of an ileocolic vein with a 24-gauge catheter (Becton Dickinson, Erembodegem-Aalst, Belgium), which is advanced into the portal vein and connected to a highly sensitive pressure transducer. The external zero reference point is placed at the midportion of the animal.

Determination of the Portal-Systemic Collateral Formation

The extent of collateral formation is measured using microspheres injected in the spleen. The animals were sacrificed and the activity of microspheres in the liver and lung tissue was calculated.

Ascites Observation and Collected Tissues

The presence of ascites is macroscopically observed and measured.

Mice are sacrificed and the inner organs are rapidly removed. Subsequently, tissue samples from liver (right, left and middle lobe), mesentery (visceral and parietal peritoneum), small intestine, duodenum, stomach, aorta abdominalis, arteria mesenterica superior and vena porta are collected for immunohistochemistry or immunoblot analysis.

Immunohistochemistry

Immunohistochemical detection of CD 31, VEGF, VEGF receptor-2 and PLGF are performed on paraffin sections from mice organs.

Western Blot and ELISA Analysis

Mice tissues are excised, immediately snap-frozen in liquid nitrogen and stored at −80° C. Measurements of CD 31, VEGF, VEGF-receptor 2 and PLGF are performed.

The invention claimed is:

1. A method to alleviate a complication of liver cirrhosis in a subject in need thereof comprising administering a molecule which prevents the interaction between placental growth factor and VEGF-Receptor 1 to said subject, wherein said molecule is an antibody against placental growth factor.

2. The method according to claim 1 wherein said complication of liver cirrhosis is portal hypertension.

3. The method according to claim 1 wherein said complication is splanchnic vasodilatation.

4. The method according to claim 1 wherein said complication is secondary biliary liver cirrhosis.

5. The method according to claim 1 wherein said complication is hypersplenism.

6. A method to alleviate liver fibrosis in a subject in need thereof comprising administering a molecule which prevents the interaction between placental growth factor and VEGF-Receptor 1 to said subject, wherein said molecule is an antibody against placental growth factor.

7. A method to decrease liver fibrosis progression in a subject in need thereof comprising administering a molecule which prevents the interaction between placental growth factor and VEGF-Receptor 1 to said subject, wherein said molecule is an antibody against placental growth factor.

* * * * *